United States Patent [19]
Anis et al.

[11] Patent Number: 5,730,718
[45] Date of Patent: Mar. 24, 1998

[54] REMOVAL OF TISSUE

[75] Inventors: Aziz Yehia Anis, 9540 Firethorne La., Lincoln, Nebr. 68520; Mark Evan Steen, Chino Hills, Calif.

[73] Assignee: Aziz Yehia Anis, Lincoln, Nebr.

[21] Appl. No.: 639,720

[22] Filed: Apr. 29, 1996

Related U.S. Application Data

[63] Continuation of Ser. No. 372,893, Jan. 13, 1995, abandoned, which is a continuation of Ser. No. 35,986, Mar. 22, 1993, abandoned, which is a division of Ser. No. 759,937, Sep. 16, 1991, abandoned, which is a continuation-in-part of Ser. No. 680,292, Apr. 4, 1991, abandoned, which is a continuation-in-part of Ser. No. 553,975, Jul. 17, 1990, Pat. No. 5,222,959.

[51] Int. Cl.$^6$ .......................... A61B 17/32; A61B 17/22
[52] U.S. Cl. .......................... 604/22
[58] Field of Search .................. 604/22, 27; 606/107, 606/127–128, 159, 166–167, 169–171, 180

[56] References Cited

U.S. PATENT DOCUMENTS

| | | |
|---|---|---|
| 464,252 | 12/1891 | Knoepfel et al. |
| 3,082,530 | 3/1963 | Hopf et al. |
| 3,526,219 | 9/1970 | Balamuth ............... 604/22 |
| 3,589,363 | 6/1971 | Banko et al. |
| 3,614,484 | 10/1997 | Shoh . |
| 3,736,938 | 6/1973 | Evvard et al. ............ 606/169 |
| 3,823,717 | 7/1974 | Pohlman . |
| 3,882,872 | 5/1975 | Douvas et al. |
| 3,976,077 | 8/1976 | Kerfoot, Jr. |
| 3,990,453 | 11/1976 | Douras et al. ........... 606/107 |
| 3,996,935 | 12/1976 | Banko ..................... 606/107 |
| 4,002,169 | 1/1977 | Cupler, II . |
| 4,167,943 | 9/1979 | Banko . |
| 4,223,676 | 9/1980 | Wuchinich et al. ...... 604/22 |
| 4,316,465 | 2/1982 | Dotson, Jr. |
| 4,320,761 | 3/1982 | Haddad . |
| 4,428,748 | 1/1984 | Peyman et al. |
| 4,445,509 | 5/1984 | Auth . |
| 4,504,264 | 3/1985 | Keuman ................... 604/22 |
| 4,515,583 | 5/1985 | Sorich ..................... 606/169 |
| 4,609,368 | 9/1986 | Dotson, Jr. |
| 4,756,304 | 7/1988 | Watanabe . |
| 4,819,635 | 4/1989 | Shapiro . |
| 4,869,715 | 9/1989 | Sherburne ............... 604/22 |
| 4,895,560 | 1/1990 | Papantonakos . |
| 4,908,015 | 3/1990 | Anis . |
| 5,019,036 | 5/1991 | Stahl . |
| 5,024,652 | 6/1991 | Dumenek et al. |
| 5,030,201 | 7/1991 | Palestrant . |
| 5,116,343 | 5/1992 | Ams et al. ............... 604/22 |
| 5,176,677 | 1/1993 | Wuchinich ............... 606/169 |
| 5,222,959 | 6/1993 | Anis ........................ 606/107 |

FOREIGN PATENT DOCUMENTS

| | | |
|---|---|---|
| 313494 | 7/1919 | Germany . |
| 2 111 390 | 7/1983 | United Kingdom . |
| WO92/01423 | 6/1992 | WIPO . |

OTHER PUBLICATIONS

"Illustrated Step–by–Step Description of the Anis Dry Extra Capsular Cataract Extraction Technique With In–the–Bag Lens Implementation"; by Azia Y. Anis; *Seminars in Opthalmology*, vol. 1, No. 2 (Jun.), 1986; pp. 113–129.

*Primary Examiner*—Michael Buiz
*Assistant Examiner*—Nancy Mulcare
*Attorney, Agent, or Firm*—Vincent L. Carney

[57] ABSTRACT

To reduce damage to surrounding tissue while fragmenting some tissue such as for example not damaging the capsular wall while removing the lens during cataract removal surgery or not damaging artery or vein walls during bypass surgery while freeing the artery or vein to be transplanted, an incision is made for the insertion of surface-discriminating, rotating, fragmenting handpiece. The surface-discriminating fragmenting handpiece fragments and permits aspiration of the tissue without damaging the surrounding wall by fragmenting surfaces of higher inertia material but moving at a rate of speed and having openings between them of such a size that the more integrated lower mass, more flexible and smoother tissue is moved away from the fragmenting zone and the higher mass, lower flexibility or rougher tissue is fragmented.

12 Claims, 6 Drawing Sheets

REMOVAL OF TISSUE

RELATED CASE

This application is a continuation of U.S. patent application filed Jan. 13, 1995, Ser. No. 08/372,893, now abandoned which was a continuation of U.S. patent application Ser. No. 08/359,864, now abandoned, filed Mar. 22, 1995, which was a division of U.S. application Ser. No. 07/759, 937, filed Sep. 16, 1991, now abandoned which is a continuation-in-part of U.S. application Ser. No. 07/680, 292, now abandoned filed Apr. 4, 1991, which is a continuation-in-part of U.S. application Ser. No. 07/553, 975, now U.S. Pat. No. 5,222,959 filed in the name of Aziz Y. Anis on Jul. 17, 1990, for Removal of Tissue.

BACKGROUND OF THE INVENTION

This invention relates to the removal of tissue from the body such as for example removal of cataracts from the eye.

It is known to remove diseased tissue from the body by fragmenting,. crushing or otherwise making the tissue flowable while in the body and then aspirating it. In one known class of surgical techniques of this type specifically intended for the removal of cataracts: (1) an incision is made along the superior corneal margin from about 10 to 2 o'clock (12 o'clock is the location closest to the top of the head of the patient) approximately 10 mm in chord length; (2) an incision is made in the capsular wall; and (3) the cataract is removed. The anterior chamber is maintained substantially formed during the operation by means of a continuous inflow of irrigating solution.

In one prior art technique of this class for removing a cataract, the nucleus is expressed out of the eye and the cortex is removed by a process of irrigation and aspiration. In another prior art technique of this class for removing the cataract, the nucleus is removed with a vectis and about 0.1 milliliter of viscoelastic compound or irrigating fluid is introduced into the capsular bag to separate the capsular walls. With the capsular walls separated, a wedge of the cortex is engaged in the aspiration port of a cannula and peeled toward the center and then aspirated to remove it. This process is repeated so that the layers of the cortex are peeled and then aspirated inwardly through the cannula, layer by layer, until the intact capsular bag (except for the horizontal incision) is completely empty and clean.

This technique of removing the cataract is disclosed by Anis, Aziz Y., "Illustrated Step-by-Step Description of the Anis Dry Extra Capsular Cataract Extraction Technique With In-the-Bag Lens Implementation"; *Seminars in Opthalmology*, v. 1, N. 2 (June), 1986, pp. 113–129 and the technique is compared with other such techniques of this class.

Two prior art types of instruments which aid in the fragmentation and aspiration of the lens nucleus to permit extraction through a small incision are disclosed in U.S. Pat. No. 3,589,363 to Anton Banko et al.; U.S. Pat. No. 3,902, 495 to Steven N. Weiss; U.S. Pat. No. 3,693,613 to Charles Kelman et al.; and U.S. Pat. No. 4,041,947 to Steven N. Weiss et al. This instrument is intended in the prior art to fragment a lens nucleus using ultrasonic vibrations to aid the irrigation/aspiration of the lens. The ultrasonic vibrations laterally reciprocate the tip of an instrument to fracture the cataract after which it can be aspirated.

A further type of instrument is disclosed in U.S. Pat. No. 4,908,015 issued to Anis on Mar. 13, 1990. This patent describes an instrument which rotates a solid member having blades extending from it to grind the lens.

These tissue removal techniques have several disadvantages, such as: (1) they risk tearing the capsular wall with the reciprocating ultrasonic vibration tools or with the rotating blades; (2) under some circumstances, they require large incisions in or removal of parts of the capsular wall; and (3) they may require the use of several different instruments.

Still another type of prior art technique for removing cataracts is disclosed in U.S. Pat. No. 3,996,935 to Banko issued Dec. 14, 1976. This type of instrument shows cooperating jaw-like members, one of which rotates inside the other to break up the lens by shearing sections of it. It aspirates fragments through the instrument. This type of instrument has a disadvantage in that it can break the capsular wall and is relatively complex. Part of the disadvantage comes from the teaching that it may be rotated manually or mechanically without a corresponding teaching of the rate of rotation required for efficient use.

Still another prior art instrument includes a small rotary magnetic cutter that is injected through the capsular wall and a means for applying magnetic fields that control the magnetic cutter in position. The small magnetic cutter is rotated as it moves from position to position in the capsular bag and to abrade or cut the lens that is to be removed.

This instrument has several disadvantages, such as: (1) it is relatively complicated and expensive because of the need to remotely control the small cutter; and (2) does not incorporate any mechanism for aspirating the lens particles as they are abraded from the lens.

In still another prior art device disclosed in U.S. Pat. No. 4,002,169, small retractable wires are rotated in a range of 5 rpm to 16,000 rpm. There is no teaching of selecting the speed for surface discrimination and the device relies on blunt surfaces to avoid damage to the capsular wall instead. This device has the disadvantages of: (1) providing a relatively slow cutting velocity range with blades not shaped for cavitation or turbulance; (2) not providing a range of velocities sufficient to form small particles that can be aspirated through a small hole; and (3) not providing for aspiration during fragmenting, thus blocking visibility with particles.

SUMMARY OF THE INVENTION

Accordingly, it is an object of the invention to provide a novel technique for tissue removal.

It is a further object of the invention to provide a novel instrument for fragmenting and removing a cataract during cataract removal surgery with low risk of damage to the capsular wall.

It is a still further object of the invention to provide a novel instrument designed to fragment tissue without damage to the nearby tissue such as for example not damaging the capsular wall while removing the lens during cataract removal surgery or not damaging artery or vein walls while removing cancerous tissue near the vein or artery.

It is a still further object of the invention to provide a novel technique for fragmenting and removing a cataract in which technique a moving fragmenting surface moves at an angle with the normal to a cataract surface, which angle is obtuse and generally close to being perpendicular to the normal in such a manner as to cause cavitation at its trailing edge to aid in fragmenting and mixing the cataract particles while maintaining the direct force on the cataract relatively low.

In accordance with the above and further objects of the invention, an incision is made for the insertion of a surface-discriminating fragmenting tool. The surface-discriminating fragmenting tool fragments and permits aspiration of high mass, rough-surface, rigid tissue without damaging nearby smooth, flexible, low mass walls. The tool fragments some tissue but avoids fragmenting other tissue by discriminating between tissues. This discrimination is based on one or more of several factors including: (1) the rigidity of the tissue; (2) the amount of mass of the tissue; (3) the angle of the tissue to the direction of movement of the tool; (4) the roughness of the surface of the tissue; and (5) the size and shape of the surface of the tissue to the extent the size and shape affect the tendency of the negative pressure created by aspiration and/or irrigation to move the tissue toward the surface-discriminating fragmenting tool.

The surface discrimination of the tool is controlled by moving surfaces which fragment diseased tissue on impact, referred to as phacotmesis, and cause cavitation forces that further fragment and mix fragments of tissue, referred to as phacocoelosis, but which move at a rate of speed slow enough so that the more integrated, more flexible, lower mass and smoother tissue is moved away without fragmenting. The tissue is not constrained by opposed shear forces of the tool as in some prior art rotating tools nor is the higher mass, rigid tissue moved significantly as a bulk.

The surfaces of the instrument fragment tissue that: (1) is stiffer and has a higher modulus of rigidity; and (2) is at an angle to the cutting edge closer to 90 degrees and receives less force moving it away. Thus, the surgeon removing a cataract adjusts the speed of movement of the tool surfaces aspirating and irrigation forces, rake angle of the leading edge and cavitation level as controlled by position of tool surface, velocity and shape of moving surface, especially the trailing edge. The adjustment is made to fragment the cortex because of its higher mass, modulus of elasticity and projections in the path of the tool surfaces but to move the capsular wall because of its lower mass, lower modulus and fewer projections closer to 90 degrees and not fragment it.

In an embodiment having a rotating tip that moves the cutting edge, the aspiration pressure is more effective within the moving surfaces of the rotating tip. It is low enough to pull the fragmented tissue and tissue to be fragmented but does not hold the smooth flexible capsular wall against movement away from the moving surfaces of the tool. The rotating surfaces move the smooth wall outwardly and provide some counter pressure to the aspirating pressure inside the fragmenting zone. In one embodiment, radially inwardly extending edges further pull and mix tissue within the fragmenting zone.

In the case of cataract removal surgery, a small incision of 2 to 7 millimeters and preferably 3 millimeters is made in the sclera along the corneal border at 12 o'clock and another incision of similar dimension or a round hole in the anterior capsular wall. The instrument is inserted and fragments the lens matter without fragmenting the capsular wall.

In the preferred embodiment, the surface-discriminating, fragmenting handpiece includes a shaft with an aspirating port in it within one or more rotating rings or loops or curved sections of a cylinder. The rotation is at a sufficient speed and the area of the open spaces between the fragmenting edges sufficiently small so that relatively smooth intact, flexible, low-inertia tissue such as the capsular wall does not remain in the path of the fragmenting surfaces because the fragmenting surfaces move it away and close the opening leading to the fragmenting zone with great frequency during the rotation while permitting the rougher or higher mass, more rigid portions of the lens to be fragmented.

The factors useful in surface-discriminatory fragmenting differ from eye to eye or tissue to tissue and may be selected in accordance with the surgeon's observations. These factors are the speed of the moving surfaces with respect to the tissue, the holding pressure from aspirating vacuum and irrigating liquid, the location and position of the moving surfaces, the rake angle of the cutting edge of the moving surfaces and the shape of the portions of the moving surfaces most related to cavitation. These factors are established by the surgeon as a function of the mass of the capsular wall and the mass of the tissue to be fragmented, the stiffness and smoothness of the capsular wall or other healthy smooth tissue and the hardness and flexibility of the tissue.

The moving surfaces of the fragmenting tool hit the cells at a substantially tangential angle and distort them or cut them with their leading edges while the trailing edges create cavitation that further breaks and mixes the tissue without imparting such force to the tissue in a direction that may injure the capsular wall. For large and rigid or for rough surfaces, the shear force and cavitation is sufficient for fragmentation whereas for more flexible, lower mass and smoother surfaces, the leading edges and the cavitation tend to move the surface away and thus avoid fragmentation. The aspirating port or ports tend to pull the fragmented material internal to the tool.

As the lens is reduced in mass and freed from its connection to the structure of the eye, its tendency to move away from the cutting edges is increased. This may be compensated for by: (1) changing the direction in which the cutting edges impact the lens sufficiently often to neutralize the tendency of the impact to move the lens in one direction; or (2) causing two cutting edges to neutralize each other by impacting the lens in opposite directions at the same time. In embodiments in which the direction is changed in a manner that prevents the lens from being caused to move by repeated tangential impacting of the lens by the cutting edges in the same direction. Without such changes in direction, the impact may cause rotation of the lens. The changes in the direction the cutting edges impact the lens may be accomplished by repeatedly reversing the motor with a reversing switch that changes the polarity of dc power applied to the dc motor from the power source so that a rotating tip changes direction of rotation. Moreover, an automatic reversing switch may be used or the tip may have a substantially linear or a curvalinear reciprocating motion applied to it to cause it to move tangentially to the surface of the lens in one direction and than in another direction, such as by applying ultrasonic or subultrasonic vibrations to the shaft holding the cutting surfaces.

In a preferred embodiment, a tubular member has a central aspirating channel along its longitudinal axis with one end having a fragmenting tip and the other end being adapted to rotate the tube. The fragmenting tip has at least one slotted fragmenting surface, with the slot extending substantially in a direction parallel to the longitudinal axis of the tube for at least a short distance. The sections between slots at the end of the tube may be bent inwardly to provide a blunt top surface or offset to form a top drill bit. The longitudinal leading edge of the slots are positioned to establish a rake angle and the surfaces may be shaped to provide a fluid pressure inwardly or outwardly to create more or less cavitation so that a tip can be selected by the surgeon in accordance with his needs.

To provide the desired cavitation, there is a blunt trailing edge shaped to increase cavitation. The leading edge offers less resistance to the lens matter and any viscous fluid in the eye or other fluid through which it moves than the trailing edge, the trailing edge being adapted to increase cavitation while the leading edge compresses, distorts and cuts the tissue that is to be removed. In one embodiment, the blunt end faces slightly outwardly from the circle of revolution of the tube to create maximum cavitation outside the shell of the tube rather than inside. The leading edge may be at an angle to provide sharpness and the adjacent wall may extend outwardly to create inward flow and hold tissue and draw tissue inwardly in cooperation with the aspirating negative pressure.

The diameter of the tube and the number of slots are selected to provide the selected amount of cavitation and cutting. The width of the slots is selected to avoid the movement of the more flexible tissue that is not to be fragmented in front the leading edge but short enough so that the heavier mass, rougher-surfaced and/or more rigid material to be fragmented does not move away because of its inertia during the rotating. In one preferred embodiment, the cavitation is at low frequency below the ultrasonic frequency range.

As can be understood from the above description, the technique and instrument of this invention have several advantages, such as: (1) they selectively fragment some tissue without damaging other nearby tissue; and (2) they are able to fragment, mix and aspirate tissue and in the case of cataract removal, also scrub the capsular wall without damaging it.

SUMMARY OF THE DRAWINGS

The above noted and other features of the invention will be better understood from the following detailed description when considered with reference to the accompanying drawings, in which.

DETAILED DESCRIPTION

Figures 1, 2:
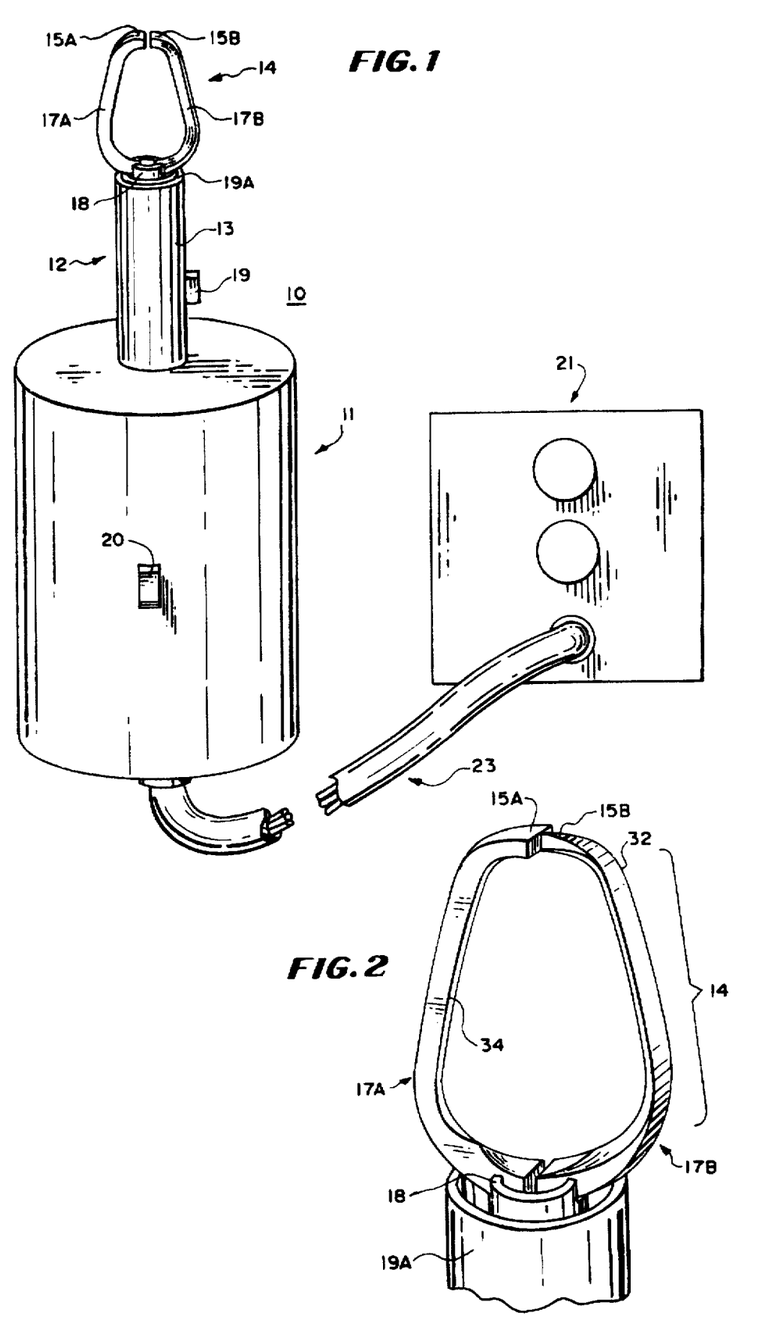
FIG. 1 is a simplified elevational view of a handpiece and control console for fragmenting and removing cataracts in accordance with an embodiment of the invention.
FIG. 2 is an enlarged perspective view of a portion of the embodiment of FIG. 1.

In FIG. 1, there is shown an elevational view of a surface-discriminating fragmenting handpiece 10, connecting tubing 23 and a console 21. The handpiece 10 includes a drive portion 11 and a surface-discriminating fragmenting tool having a blade portion 14 and a tubular sleeve portion 12. The tubular sleeve portion 12 includes a tubular casing 13, and an inner tabular aspirating drive shaft or sleeve 18. The drive portion 11 houses the motor, an on-off switch 20 and connectors for irrigating fluid and aspirating vacuum pressure.

The blade portion 14 includes blades 17A and 17B each of which is fastened to the rotatable tubular shaft 18 at diametrically opposite locations on the shaft and each of which has a corresponding one of the blunt tips 15A and 15B turned inwardly to avoid cutting. The outer sleeve 13 includes within it a movable sleeve 19A so that upon longitudinal movement of the button 19 with respect to the outer casing 13 of the tubular sleeve portion 12, the blades 17A and 17B move apart in a fragmenting position in response to one direction of movement of the shaft 19A and are forced within the movable sleeve 19A within the tubular sleeve 12 against the pressure of the spring-like blades upon movement in the other direction to fit within a smaller incision such as a 2 millimeter opening. The blades 17A and 17B are narrower in the direction of rotation and blunt on the trailing edge to cause cavitation. .pa With this arrangement, the blades 17A and 17B may be moved together for insertion of the handpiece 10 into the capsular sack through a relatively small aperture and then permitted to expand outwardly so that the upon rotation of the blade portion 14 of the tool section the cortex and nucleus are fragmented within the capsular sack. In the embodiment of FIG. 1, the handpiece 10 includes a motor for rotating the shaft and a tubular connector 23 for aspirating fragments. The console 21 may include for cooperation with the handpiece 10, a standard source of electrical power, a vacuum source, a source of irrigating liquid and a pump for irrigating liquid. These elements are conventional and are not part of the invention except insofar as they cooperate with the handpiece 10.

In FIG. 2, there is shown an enlarged fragmentary perspective view of the blade portion 14 of the tool assembly having first and second blades 17A and 17B with corresponding blunt ends 15A and 15B. The blades 17A and 17B are sufficiently flexible in the embodiment of FIG. 2 to expand until they form outwardly curved cutting surfaces extending beyond the surfaces of shaft 13 (FIG. 1) and have sharpened edges 32 and 34 tangentially to or pointing inwardly from the circles of rotation formed as they rotate. When the blades 17A and 17B are pulled inwardly by movement of the sleeve 19A upwardly, they fit within a cylinder having a diameter of less than 2 millimeters.

While the embodiment of FIGS. 1 and 2 have blades with sharpened edges pointing tangentially to or inwardly from the direction of rotation, sharpened edges are not necessary and the angle of attack or rake angle of the sharpened edges when they are part of an embodiment may vary. However, the angle of attack may be tangential to the path of rotation or any angle on either side. For this purpose, any one of several multiple blade assemblies 12 with their attached inner drive shaft 18 may be inserted into the sleeve portion 12 and drive portion 11. The blade portion is selected by the physician and one fact in such selection is the angle of attack of the blades.

To permit compressing of the blades 17A and 17B into a protective sleeve, the tubular sleeve portion 12 includes three coaxial sleeves 18, 19A and 13 (FIG. 1) in that order outwardly from the central axis. The blades are mounted to tubular drive sleeve 18 for rotation therewith and there is a space between sleeves 18 and 19A for irrigating fluid to flow. The sleeve 19A is affixed to the button 19 (FIG. 1) and moveable axially with respect to sleeve 13 to engage the blades 17A and 17B and compress them inwardly.

Figures 3, 4, 5:
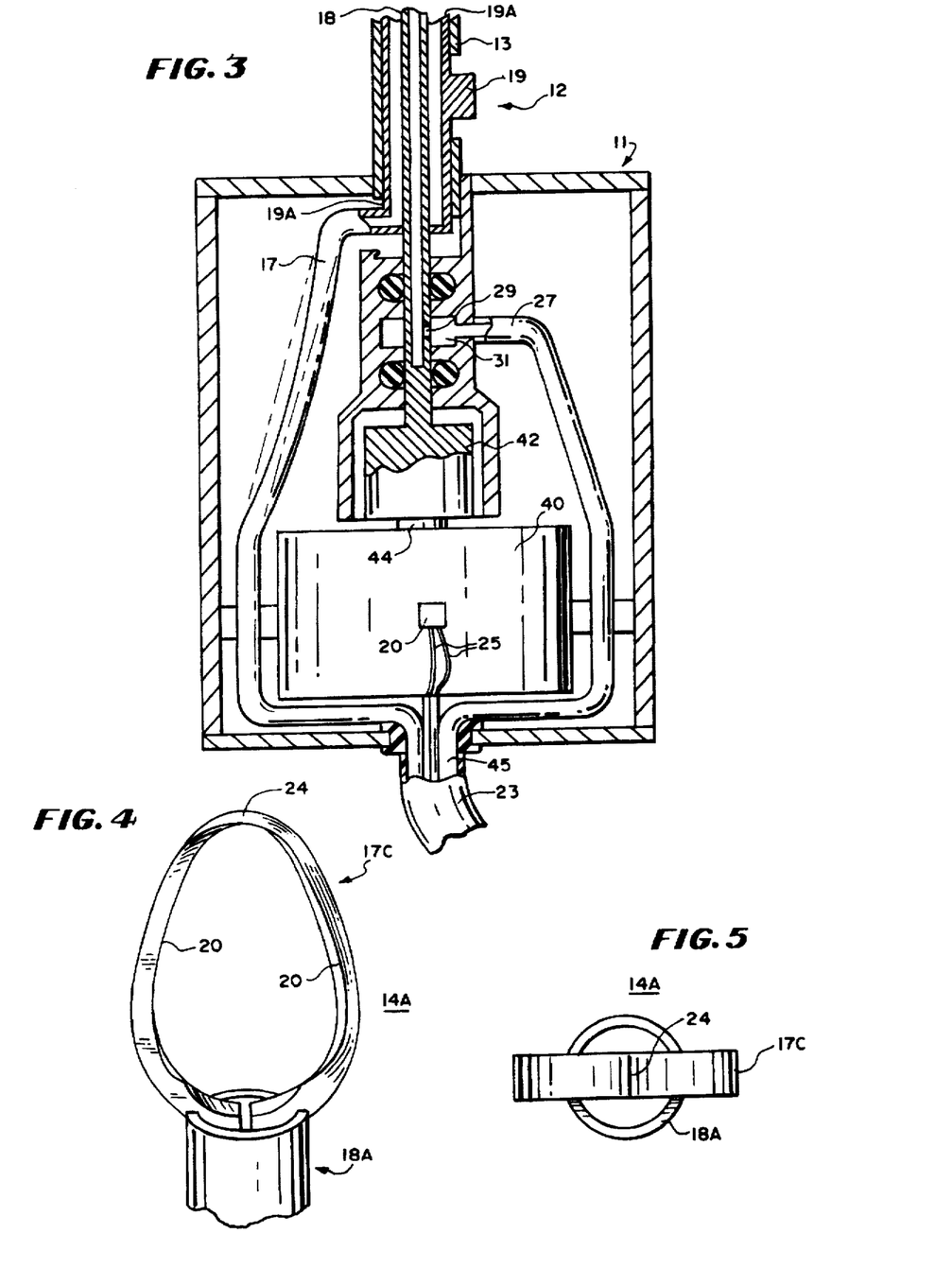
FIG. 3 is a fragmentary sectional view of another portion of the embodiment of FIG. 1.
FIG. 4 is a fragmentary perspective view of another embodiment of blade portion usable as a replacement for the blade portion in the embodiment of FIG. 1.
FIG. 5 is a plan view of the embodiment of FIG. 4.

In FIG. 3, there is shown a fragmentary longitudinal sectional view of the sleeve portion 12 and drive portion 11: (1) having within the sleeve portion 12 the rotatable tubular aspirating drive shaft 18, the tubular protective sleeve 19A and the outer sleeve 13; and (2) having within the drive portion 11, a motor 40 for rotating the aspirating drive shaft 18 to turn the blades 17A and 17B, (FIG. 1) a hollow aspirating tube 27 to apply vacuum pressure to the interior of the shaft 18, an irrigating tube 17 communicating with the tube 19A to apply irrigating fluid through the tube 19A and electrical wires 25 to control the motor 40. The shaft 18 is coupled at one end 42 to the output shaft of 44 of the motor 40 for rotation therewith and to the tubular connection 45 for aspiration.

As shown in this view, the outer wall 13 supports within it a movable wall 19A with a button extending through a slot in the outer wall 13 by which the wall 19A may be moved upwardly and downwardly to bend the blades 17A and 17B inwardly for retraction or permit them to expand outwardly in the cutting position to their normal position for rotating and in some embodiments still further under centifugal force when rotating. However, the moment of inertia of the blades is sufficient so that the centrifugal force does not force the points to point outwardly and only the bent flat surface is presented to the outer wall during rotation. It is spaced from the movable tube 19A to permit irrigating fluid to flow therebetween and contains in its center the opening 15 which extends downwardly for aspiration of tissues.

To provide irrigating fluids, the conduit 17 is connected through the cable 23 to the console 21 (FIG. 1) from which irrigating liquid is pumped through the conduit 17 around the motor 40 and to the space between the movable tube 19 and shaft 18 to supply irrigating fluid to the capsular sack. To aspirate tissue, the central opening 15 in the shaft 18 passes through an opening 29 in the wall of the shaft 18 and communicates through the sealed circular ring 31 with the aspirating conduit 25. The conduit 25 passes around the motor 40 and through the cable 23 to the console 21 which applies slight negative pressure to aspirate tissue. The cable 23 also carries electrical conductors for the motor 40 which are connected in series between the switch 20, and a source of electrical power in the console 21 and the motor 40.

To use the embodiment of FIGS. 1–3, an incision is made for the insertion of the surface-discriminating fragmenting handpiece 10. The surface-discriminating fragmenting handpiece 10 fragments and permits aspiration of the tissue but avoids damaging nearby smooth, flexible walls. Instead it fragments rougher, more rigid surfaces of higher masses. This surface discrimination is controlled by the moving surface of the blades 17A and 17B which permit the diseased tissue to be strained or cut by the blades and further fragmented by the forces of cavitation within their fragmenting zone but which move at a rate of speed and have openings between them of such a size that the more integrated, lower mass or more flexible and smoother tissue does not fall within their fragmenting zone but is moved away the moving surfaces. The aspirating pressure, cavitation and turbulence is counteracted or attenuated within the sphere of the rotating ring to avoid damage to the flat surface tissue.

In the case of cataract removal surgery, a small incision of 2 to 7 millimeters and preferably 3 millimeters in the schlera along the corneal border at 12 o'clock and another incision of similar dimensions in the capsular wall. The instrument is inserted and fragments the higher mass, more rigid, rougher lens without fragmenting the capsular wall.

The actual time that the fragmenting zone must be open to fragment diseased tissue without injuring smooth walls differs from eye to eye or tissue to tissue and may be selected in accordance with the surgeon's observations prior to use. It is a function of: (1) the rigidity of the tissue; (2) the mass of the tissue; (3) the angle of the tissue to the direction of movement of the tool; (4) the roughness of the surface; and (5) the effect of the negative pressure pulling the tissue inwardly such as the aspiration vacuum pressure which may vary in its effect depending on the size and shape of the tissue.

The surface discrimination of the tool is controlled by moving surfaces which cause the diseased tissue to fragment under impact, referred to as phacotmesis, and cavitation forces, referred to as phacocoelosis, but which move at a rate of speed slow enough so that the more integrated, more flexible, lower mass and smoother tissue is moved away without fragmenting. The surfaces of the instrument fragment tissue that: (1) is stiff; (2) has a high mass and large inertia; and (3) is at an angle to the cutting edge close to 90 degrees.

To take advantage of the differences between the tissue to be fragmented and the lower, more flexible tissue, the surgeon removing a cataract adjusts the speed of movement of the tool surfaces, the aspirating and irrigation rates, the rake angle of the leading edge of the blade surfaces and the cavitation level as controlled by position of blade surfaces, the velocity and the shape of the moving surface, especially the trailing edge of the blades. The adjustment is made to fragment the cortex because of its higher mass, modulus of elasticity and projections in the path of the tool surfaces but to move the capsular wall away from the blades because of its lower mass, lower modulus and fewer projections closer to 90 degrees. Tips are replaced to change the rake angle and cavitation surfaces.

The aspiration pressure is more effective within the moving surfaces of the rotating tip. It is low enough to pull the fragmented tissue and tissue to be fragmented but does not hold the smooth wall against movement nor pull it inwardly. The rotating surfaces move the smooth wall outwardly and provide some counter pressure to the aspirating pressure inside the fragmenting zone. In one embodiment, radially inwardly extending edges further pull and mix tissue within the fragmenting zone.

To better describe this and other embodiments, some special terminology is useful. For purposes of this description, the words, "low power" means less than one horsepower (1.341 kilowatts). In this description, the words, "motion resistance" means the resistance of a portion of tissue to movement when impacted by a moving tool surface caused by the inertia of the tissue and the effect of the inertia of other tissue connected to it taking into consideration the flexibility of the connecting tissue.

In this description, the words, "fragmenting velocity", means the minimum velocity of a moving surface of a tool with respect to predetermined stationary tissue that the moving surface of the tool impacts which fragmenting velocity is sufficient to cause strain in the tissue of at least ten percent of the distance moved by the entire tissue mass and to break the tissue by combined strain, cutting and cavitation effects when: (1) the predetermined stationary tissue has a predetermined motion resistance; and (2) the tool surface has sufficient kinetic energy to maintain its velocity constant in spite of the impact. The fragmenting velocity is affected by: (1) the angle the motion of the moving surface makes with the surface of the tissue; and (2) the momentum of the moving surface.

In the embodiments of FIGS. 1–3, a ring or partial ring having a diameter of 2 millimeters in the widest distance perpendicular to the axis of revolution forms a surface of revolution when rotated having at any one time open spaces and a solid cutting ring. The ring is rotated at approximately 120,000 rpm (revolutions per minute). The solid ring is approximately 0.50 millimeter wide along the surface of revolution, leaving an open area in the surface of slightly less than 9 square millimeters and more precisely 8.9 square millimeters with a length of 2.4 millimeters at the longest circle of a segment.

The time between portions of the solid ring sweeping across any surface of revolution is approximately every 250 microseconds and should be no longer than once every 3 milliseconds (1,000 rpm) but may be as short as 0.75 microsecond (400,000 rpm). With this arrangement and with parameters adjustable for the particular circumstance, the capsular wall does not enter into the fragmenting zone within and near the surface of revolution and is not cut and yet the ring is able to fragment the lens for easy aspiration.

In FIG. 4, there is shown a second embodiment of blade portion 14A having a shaft 18A connected to a blade 17C formed as a partial zone of a circle or an arc extending from the shaft 18A and having a pear-shaped, blade portion with: (1) blunt trailing edges 20; (2) sharpened inner edges 22; (3) a wide base attached to the shaft and narrower along the axis of the tube 18A so that there is at the wide portion a blunt trailing edge and a sharpened leading edge as the cutting blade rotates about the shaft 18A; and (4) an axis of rotation along the shaft 18A between the base and the narrower upper portion. The apex is generally blunt, but in some embodiments has a drill shape at the apex 24.

It has been found that the sharpened edges strain and elongate the cells of higher mass rigid material but push away flexible and low mass material. The leading edges under some circumstances cut or scrape fine particles from the harder material that might otherwise plug the aspirating channel but the cavitation effect fragments the particles into small particles that can easily be aspirated. The blades are shaped to maximize cavitation that liquifies and stresses lens matter and any viscous fluids and causes fragmentation and mixing of the higher-mass more rigid material. In the embodiment of FIG. 4, the blades have two blunt sides and a top blunt portion 24 and at the mounting base to the tube 18A for strength at the bottom and to form a non cutting surface at the top.

In FIG. 5, there is shown a top view of the embodiment of FIG. 4, having a portion 14A with a blade 20B shaped with a thicker portion having a blunting surface 24 at its upper end facing away from the direction of the tubular shaft 18A and rotating thereabout. However, in some embodiments it has a cutting edge to permit it to provide an abrading center area in the forward direction for positioning at a point to be fragmented. This embodiment operates substantially the same as the prior embodiments except that its unique shape enables careful placement for special purposes. Instead of a cutting edge, the top portion 24 may be bent inwardly or may be blunt to avoid cutting at its top.

Figure 6:
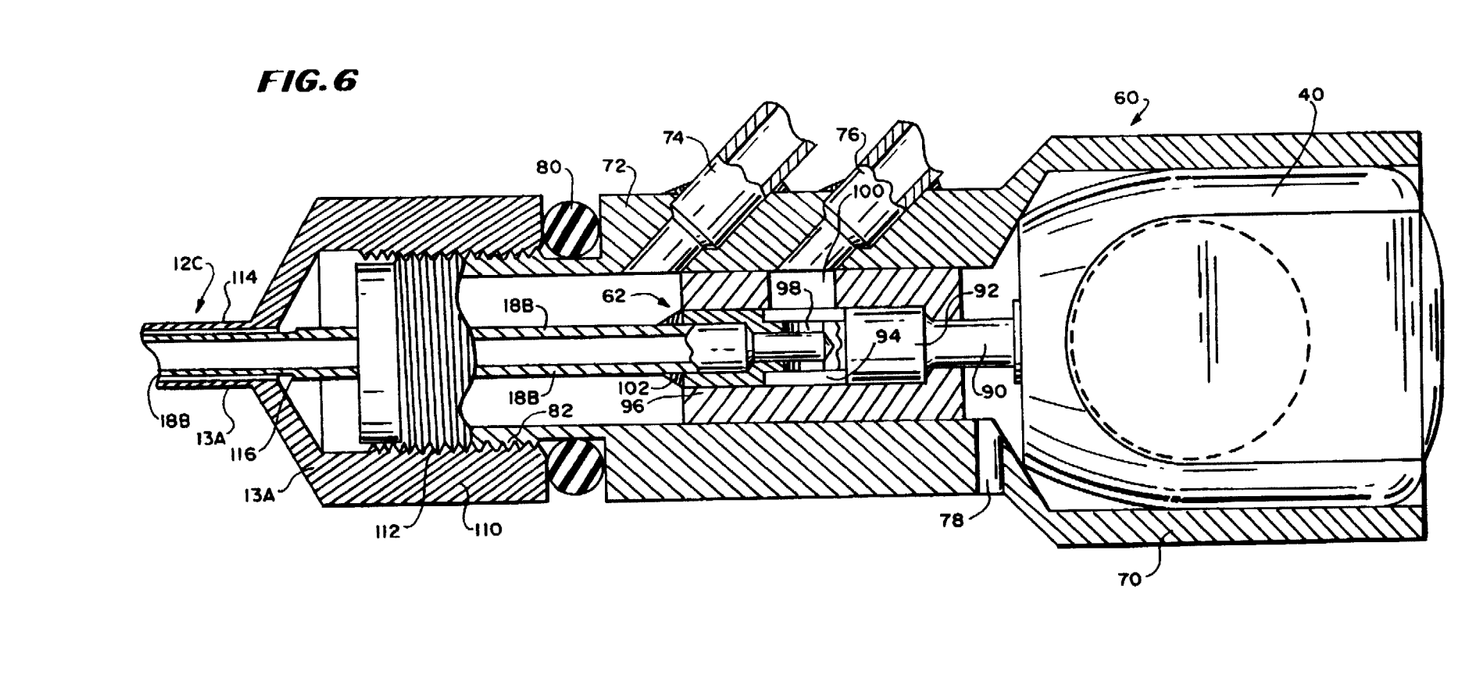
FIG. 6 is a fragmentary elevational view, partly sectioned and partly diagramatic of another embodiment of handpiece.

In FIG. 6, there is shown a fragmentary, partly diagramatic and partly longitudinally sectioned view of another embodiment of hand tool 10A which is operated by a similar dental drill motor 40 and adapted to receive a tool by having inserted therein the aspirating tube 18B of the sleeve portion 12C substantially identically to that of the embodiments of FIGS. 1–5 except that the blade portion is constructed in a different manner on the end of the shaft 18 as will be described hereinafter.

The hand piece 10A includes in addition to the aforementioned motor 40, an aspirating drive sleeve 18B, an outer housing 60 and a motor-tool sleeve coupling 62 with: (1) the motor 40 being connected to the tool sleeve 18B through the coupling 62 and being located within the housing 60; (2) with the sleeve 18B extending outwardly thereof for rotation by the motor 40 through the coupling 62 during operation of the hand piece.

To enclose and provide the necessary liquid and vacuum connections to the operative tool, the housing 60 includes a motor housing portion 70 and a tool and coupling housing portion 72 integrally formed together with tubular connectors 74 for irrigating fluid, tubular connector 76 for aspirating negative pressure and hole 78 for air venting being provided through the housing 60. The air vent port 78 is an opening extending into and communicating with the interior of the motor housing portion 70 to provide cooling to the motor 40. The irrigating fluid connector is an opening communicating with the interior of the housing portion 72 to apply fluid therethrough for eventual passage through the protective sleeve 13A on the outside of the tooling sleeve 18B and to the operating point in a manner to be described more fully hereinafter.

The aspirating connecting opening 76 is adapted to receive tubing for applying negative pressure through the motor-tool coupling 62 to the interior of the tooling shaft 18B to withdraw material during use of the hand piece. The forward end of the housing portion 72 includes external threads 82 which engage internal teeth on the protective sleeve 13A and a shoulder with an O-ring 80 positioned in it so that, the protective sleeve 13A can be threaded onto the housing 60 to enclose a portion of it sealingly and extend through its outer end in a manner to be described hereinafter.

To connect the motor 40 to the sleeve portion 12B, the motor-tool sleeve coupling 62 includes the motor output shaft 90, a cylindrical boss 92, a cylindrical support member 94, an annular groove 96 within the boss 92, two counter bores 98 through the boss 92 at the bottom of the annular groove 96, an opening 100 communicating with the aspirating connector 96 and extending through the cylindrical support 94, a cylindrical opening 95 sized to receive the sleeve 18B and a brazed connection 102 more firmly fastening the boss 92 to the sleeve 18B. The support 100 receives the motor shaft 90 and the boss 92 which rotate within it and are supported by it. The groove 96 communicates with the opening 100 as it rotates because of its annular shape and receives vacuum pressure which it transmits through the openings 98 into the sleeve 18B to create negative pressure in the working tip through this elongated sleeve.

With this arrangement, the sleeve 18B is rotated and carries vacuum pressure with it to the tip. The brazed connection 102 aids in transmitting force from the output shaft 90 to the shaft 18B through the boss 92 by increasing the firmness of the connection between the tool sleeve 18B and the shaft 80.

To mount and support the tool sleeve 18B, the protective sleeve 13A in the embodiment of FIG. 6 includes a cylindrical base member 110 having internal teeth 112 adapted to engage the internal teeth 82 of the housing 72 and is sealed against the flow of fluid therethrough by the O-rings 80 compressed between the enlarged cylinder 110 and the housing portion 72. A narrower outer sheath portion 114 is intergrally formed with the cylindrical portion 110 and receives a cylindrical passageway formed between the inner tool sleeve 18B and its outer tubular surface to permit the flow of irrigating liquid between the outer protective sleeve 13A and the inner member tool sleeve 18B into the capsular bag.

With this arrangement, the tool sleeve 18B can be rotated by the motor 40 and at the same time: (1) irrigating fluid can be applied between it and the protective outer sleeve 13A; and (2) aspirating negative pressure can be applied to pull fragments along its longitudinal axis. At its outer end, the fragmenting tip or blades are formed in a manner to be described hereinafter.

Figure 7:
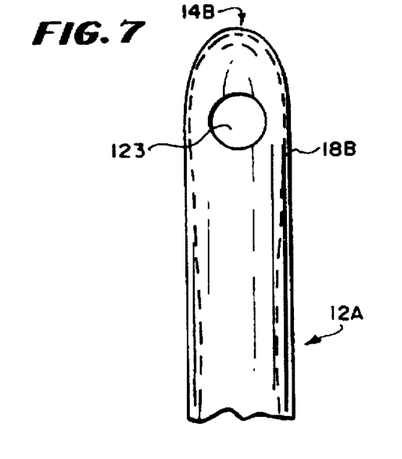
FIG. 7 is a fragmentary elevational view of another embodiment of tool portion.

In FIG. 7, there is shown a front elevational view of one embodiment of a tool having a sleeve portion 12A and a blade portion 14B with two blade members formed in its outer end and separated by an opening 120 longitudinally passing along the longitudinal axis of the tool to form blade portion 14B at the end of the same cylinder forming the sleeve 12A. Both the blade portion 14A and sleeve portion 12A are formed on a single integrally formed cylinder that serves as the aspirating drive shaft 18B. Aspirating holes extend through the tip of the blade portion 14A orthogonal to the longitudinal axis and the slot 120. To receive some material for aspirating, the aperatures 122 and 123 are approximately 0.04 inch from the tip 24 of the blade portion 14A and the diameter of the tube 18B is approximately 0.042 inch. The diameter of the aspirating holes 122 and 123 is 0.018 inch and should not be larger than 7 millimeters.

Figure 8:
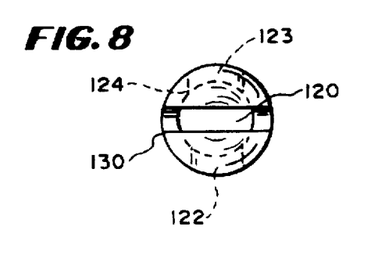
FIG. 8 is a top view of the embodiment of FIG. 7.
Figure 9:
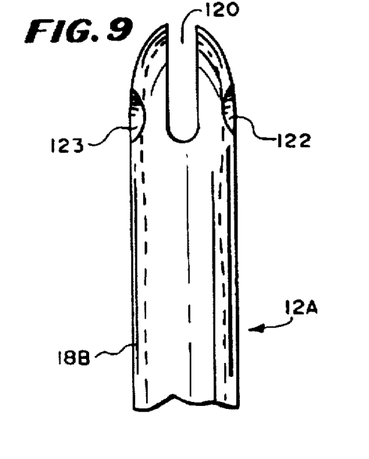
FIG. 9 is an elevational right hand view of the embodiment of FIG. 7.

FIGS. 8 and 9 are a plan view and a right elevational view of the embodiment of FIG. 7, respectively, showing the slot 120 having a width of 0.008 inch and extending downwardly approximately 0.07 inch. As best shown in FIG. 8, the edges of the walls of tube or sleeve 18B along the slot have a larger or blunter trailing edge shown at 126 and a sharper leading edge at 124 in one embodiment as well as a blunter edge at 130 and a sharper edge at 128 so that the sharper edges as the item rotates counter-clockwise as shown in FIG. 8 elongate or cut the tissue within the eye and create cavitation at the blunter edge.

Figure 10:
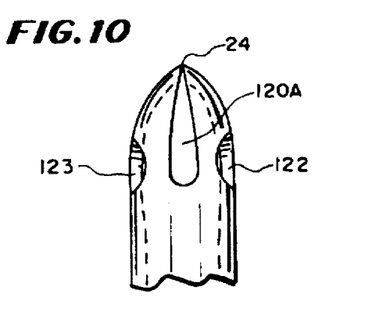
FIG. 10 is a fragmentary elevational view of a tool tip which represents a variation of the tool tip of FIGS. 7–9.

In FIG. 10, there is shown a fragmentary front elevational view of another embodiment showing the tip along the slot brought together, welded and offset to provide a sharper and a blunter edge by offsetting the edges along the slot to a greater degree but without the need for changing the thickness of the tube walls. This embodiment forms a rake angle of 90 degrees and two cutting edges but slots at three locations in the wall of sleeve 18B can also be formed instead of two slots 180 degrees apart, providing a 60 degree rake angle and three cutting edges or four slots to provide a 45 degree rake angle and four cutting edges. Moreover, the tips can be brought together as in FIG. 10 to form a smooth protective dome or can include a cutting edge or be open. The tip can also be twisted, which will change the rake angle along the slot and provide a cyclone fan pulling effect.

Figure 11:
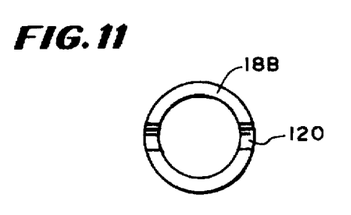
FIG. 11 is a diagramatic top view of a tool tip illustrating a first step useful in making the embodiment of FIGS. 7–9.
Figure 12:
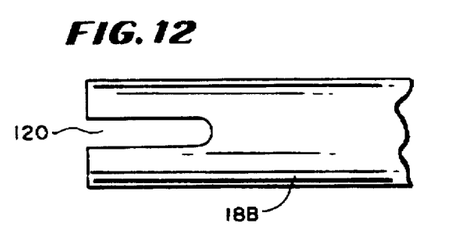
FIG. 12 is a fragmentary elevational view of the tool tip shown in FIG. 11.
Figure 13:
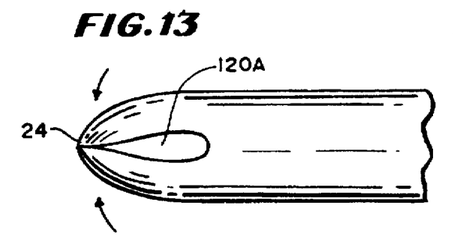
FIG. 13 is an elevational view of a tool tip illustrating a second step in preparing the embodiment of FIGS. 7–9.
Figure 14:
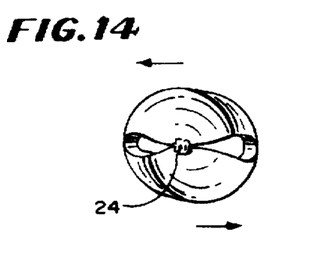
FIG. 14 is a top view of the tool tip shown in FIG. 13.

To form the embodiments of FIGS. 7–10, a tubular sleeve is slotted at 120 as shown best in FIGS. 11 and 12 and pinched together. The two sides are then offset in space laterally in a direction along a plane passing through the center of the slots and the longitudinal axis of the sleeve as shown in FIGS. 13 and 14 and the tips pinched together and brazed together to form a tip such as that shown in FIG. 10. Prior to closing the tips 140, the narrower and blunter edges may be further shaped by cutting one wall at a more acute angle than the other wall and then removing the other sides of the slot with a reverse cut so as to form flat cuts and sharpened cuts.

Figure 15:
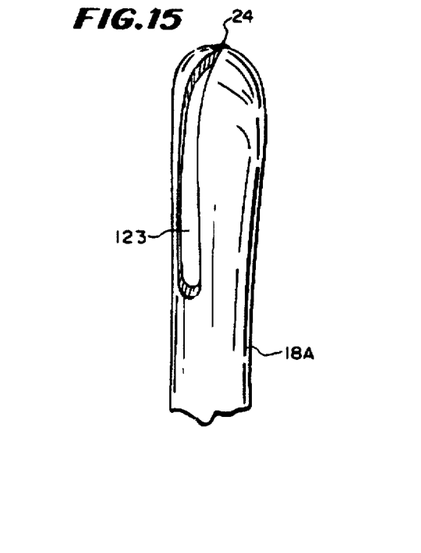
FIG. 15 is a fragmentary perspective view illustrating an additional step in preparing the embodiment of FIGS. 7–9.
Figure 16:
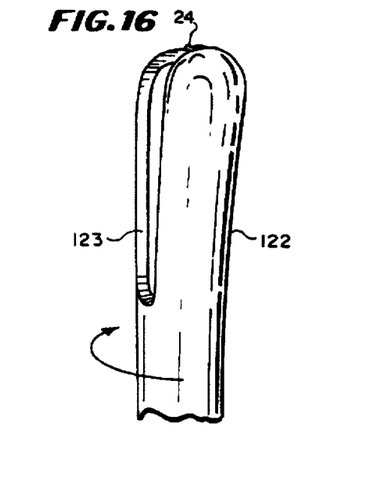
FIG. 16 is a perspective view illustrating still another possible step in preparing a tool tip similar to the embodiment of FIGS. 7–9.

To form other raking angles and shape the blade to pull viscous fluid or such viscous fluid, the ends are offset, twisted and brazed as shown in FIG. 15 and 16, first offset along a line or plane aligned with the two slots and longitudinal axis and then twisted at a slightly different angle to form a different rake angle and cyclone pump effect. The tip is normally smooth at the very tip 140 but has a cutting effect as it moves radially outwardly.

In one version of the preferred embodiment, the tube has an outer diameter of 42 thousandths (0.042) inch with two diametrically opposed slots. The ends are moved together in a curvature leaving a slot about 8 thousandths inch wide at its widest point and extend from the top approximately 70 thousandths inch (70 thousandths long). Ninety degrees removed from the two slots are central aspirating apertures having a diameter of 18 thousandths of an inch and being circular in cross section. They are located with their bottom edge generally adjacent to the end of the slots.

The tube usually rotates at approximately 1600 hertz when fragmenting the nucleus in a preferred embodiment having two cutting edges and the wedged surfaces of the slots have one edge that is in a range of 1 thousandths of an inch to twenty thousandths of an inch thick and a trailing edge that is in the range of ten thousandths of an inch to fifty thousandths of an inch thick. Preferably, it should be in the range of 300 hertz to 4000 hertz but may be slower or faster when at a location in the capsular sac not near tissue to be preserved or which may be moved to change other tissue. The slots and rate of rotation are selected to provide, in the preferred embodiment, a surface moving 200 centimeters a second at the fastest point on the curved moving surfaces and preferably to provide a surface moving at the fastest point within a range of 5 meters a second to 40 centimeters per second at the fastest point but may move slower or faster under some circumstances.

Since it is a rotating surface which curves inwardly toward the center, the speed is very low at the center and under some circumstances does little fragmenting at the center and more and more fragmenting as the rotating radius increases to the sleeve radius. The slot is next to tissue for a very short time such as between 10 milliseconds and 1 millisecond. Each cutting edge sweeps past a point about once every 625 microseconds, preferably, or in the normal range of once every 3 milliseconds to once every 400 microseconds.

In addition to zones of a sphere and sections of a cylinder intended for use within an eye, other shapes of moving surfaces may be used and the tool has uses other than for cataract removal such as in vascular operations. For example, multiple zones of a sphere may be spaced from each other at a shorter distance so that the item need not be rotated as fast and motion other than rotational motion may be used to prevent entrance of the tissue into the fragmenting zone. A convenient embodiment for removing structures around veins or arteries during vascular operations is dumbell shaped so that a recess fits around the vein while spherical cutting zones are positioned on either side of the vein.

In some embodiments, the moving surface is formed of a curved member attached to a rotatable shaft having a sharpened edge at an angle of between 0 and 60 degrees but preferably 45 degrees with a surface of revolution which surface has a center of rotation aligned with the rotating shaft. The sharpened edge of the curved member may face away from the center of rotation so that the cutting action of the sharpened surface is into the cortex and core material of a cataract.

Figure 17:
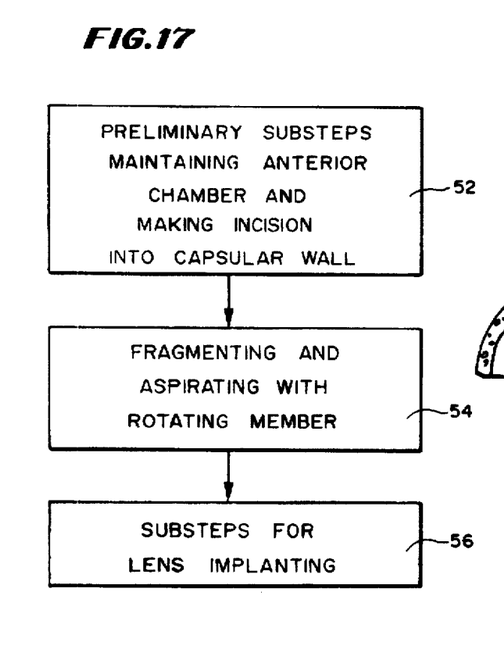
FIG. 17 is a block diagram of a process for using the instrument of FIGS. 1 through 6 to remove a cataract.
Figure 18:
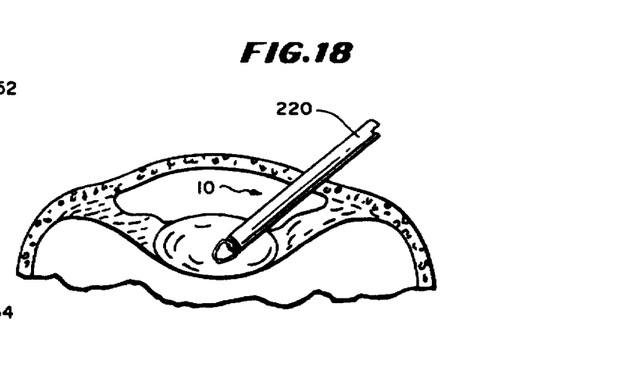
FIG. 18 is a simplified cross-sectional view of an eye and cataract removal handpiece tip illustrating a portion of the technique of this invention.

In FIG. 17, there is shown a block diagram generally illustrating the steps in a cataract extraction and lens implantation technique 50 comprising: (1) the step 52 which includes the preliminary substeps of maintaining the anterior chamber and making the incision into the capsular wall; (2) the step 54 of fragmenting and removing the lens; and (3) the step 56 which includes the substeps necessary for implanting the lens.

In performing this technique, the step 52 which includes the substeps required to make the incision and maintain the anterior chamber and the step 56, which includes the substeps necessary for implanting are not by themselves new and many of the steps are described in Anis, Aziz Y., "Illustrated Step-by-Step Description of the Anis Dry Extra Capsular Cataract Extraction Technique With In-the-Bag Lens Implementation", *Seminars in Opthalmology*, v. 1, N. 2 (June), 1986, pp. 113–129. Moreover, the removal of the lens may not be followed by implantation but may be part of a treatment in which the aphakia is treated by contact lens or glasses.

The step 54 of fragmenting and removing the lens includes: (1) the step of inserting the handpiece; (2) the step of extending the blades in some embodiments within the capsular bag; and (3) the step of breaking and removing the hardened part of the nucleus. These steps are all performed through a small incision while the anterior chamber is maintained with a viscoelastic medium. Hydrodelineation may be performed as described in U.S. Pat. No. 4,908,015, if desired, but such hydrodelineation is not part of this invention.

The step 52 which includes preliminary substeps of maintaining the anterior chamber and making the incision in the capsular bag includes the substep of making a small incision in the capsular bag, preferably no greater than 3 millimeters in length and in the range of 1 to 2 millimeters. This incision is made while the anterior chamber is maintained and is made as small as possible to maintain the structure of the capsular bag to the extent possible. Through this small incision, the step 54 of fragmenting and removing the lens and the step 56 of implanting a lens are performed. Under some circumstances, the incision may be 4 or 5 millimeters but should always be less than 7 millimeters.

With the posterior capsule in focus in the focal plane of the microscope, the handpiece 10 is introduced through an incision shown at 220 in FIG. 13 in the wall of the capsulary sac. The tip of a handpiece 10 is thrust through the incision in the wall of the capsular bag and into the lens therein.

The blades are rapidly rotated while slight negative pressure is applied to aspirate the fragments. The rotating blades are inserted gradually into the cortex and nucleus and from time to time a small amount of irrigating fluid is injected. Fragmented cortex or nucleus material is aspirated. After removal of the cataract and the handpiece with the capsular sac relatively intact, a lens implant is inserted through a relatively small opening as described in the above publication of Anis.

Generally, the nucleus is first removed then the cortex. The surface-discriminating fragmenting handpiece fragments and permits aspiration of the cotex and nucleus without damaging nearby smooth walls of the capsular sac. It avoids fragmenting the smooth walls with its cutting edges but fragments rougher, stiffer higher mass tissue, moving it into a negative pressure zone for aspiration. The smooth more flexible, lower mass surfaces are moved by the blades which hit it at an angle. The tissue being fragmented is hit at an angle and subject to cavitation rapidly and repeatedly with a force each time that does not move the entire material to the extent that it may damage the capsular wall or other healthy tissue that is not to be fragmented but does fragment the cortex.

The surface discrimination of the instrument is controlled by moving surfaces which permit the diseased higher mass tissue to be fragmented but which move at a rate of speed and have openings between them of such a size that the more integrated flexible, lower mass and smoother tissue does not fall within their fragmenting zone. The tissue is not constrained by opposed shear forces of the instrument but are free to move and the cutting edge of the instrument cuts tissue that: (1) is stiffer and has a higher modulus of rigidity; and (2) is at an angle to the cutting edge closer to 90 degrees and receives less force moving it away.

Thus, the surgeon removing a cataract adjusts the speed of movement of the cutting edge to cut cortex with a higher mass and modulus and more projections in the path of the cutting surface and not the capsular wall with a lower modulus and mass and fewer projections closer to 90 degrees so it is more readily moved away from the cutting edge. The aspirating pressure is low enough to pull the fragmented tissue but not the smooth wall. The rotating surfaces move the smooth wall outwardly and provide some counter pressure to the aspirating pressure inside the cutting zone.

In using this instrument, as the lens is reduced in mass and freed from its connection to the structure of the eye by fragmentation, its tendency to move away from the cutting edges is increased. One way of compensating for this effect may be by changing the direction in which the cutting edges impact the lens sufficiently often to neutralize the tendency of the impact to move the lens in one direction. The direction is changed in a manner that prevents the lens from being caused to move by repeated tangential impacting of the lens with the cutting edges in the same direction. Without direction changes, such impacting may cause the lens to move, such as by causing rotation of the lens. Another way is by impacting the lens simultaneously in opposite directions.

The changes in the direction from which the cutting edges impact the lens may be accomplished by the repeatedly reversing the motor with a manual reversing switch that changes the polarity of dc power applied to the dc motor from the power source so that a rotating tip changes direction of rotation. Moreover, an automatic reversing switch may be used or the tip may have a substantially linear reciprocating motion back and forth or a curvalinear reciprocating motion applied to it to cause it to move tangentially to the surface of the lens in one direction and then in another direction, such as by applying ultrasonic or subultrasonic vibrations to the shaft holding the cutting surfaces.

Figure 19:
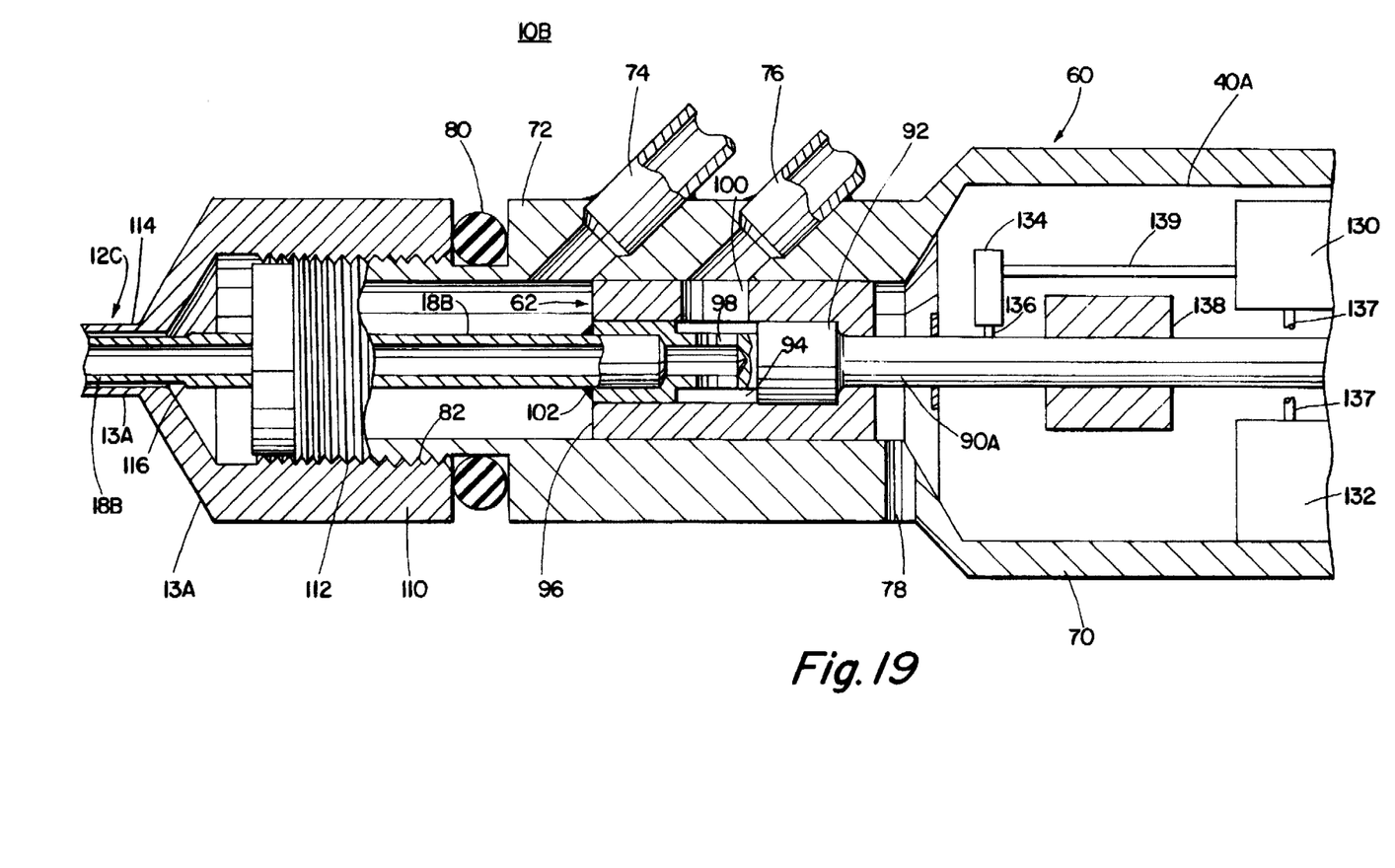
FIG. 19 is a fragmentary elevational view, partly sectioned and partly diagramatic of still another embodiment of handpiece.

In FIG. 19, there is shown a fragmentary, partly diagramatic and partly longitudinally sectioned view of still another embodiment of hand tool 10B especially useful after the lens has been reduced in size. Instead of being operated by a dental drill motor 40, it is driven by a vibrator 40A, which may be any conventional type of vibrator such as those used to operate the tip in the above-mentioned U.S. Pat. Nos. 3,589,363 to Anton Banko, et al., 3,902,495 to Steven N. Weiss, 3,693,613 to Charles Kelman, et al, and 4,041,947 to Steven N. Weiss, et al. Except for the drive mechanism, the handpiece is identical to the embodiment of FIG. 6 and the reference numbers for identical parts remain the same.

The handpiece 10B includes, in addition to the aforementioned vibrator 40A, an aspirating drive sleeve 18B, an outer housing 60 and a motor-tool sleeve coupling 62 with: (1) the vibrator 40A being connected to the tool sleeve 18B through the coupling 62 and being located within the housing 60; (2) with the sleeve 18B extending outwardly thereof for vibrating curvalinear motion by the vibrator 40A through the coupling 62 during operation of the handpiece.

The vibrator 40A includes a conventional oscillator 130, source of dc power 132, and piezoelectric or electromagnetic vibrator 134 electrically connected in series with the switch 20 (FIG. 1) to be energized and vibrate the cutting edges (not shown in FIG. 19) connected to the shaft 12C as explained in connection with the embodiment of FIG. 6. The shaft 90A is mounted for rotation in bearings 138 and includes a welded arm extending orthogonally and radially therefrom, biased into contact with or fastened to a movable portion of the vibrator 134 so that vibration of the vibrator imparts rotating motion to the shaft 90A.

To connect the vibrator 40A to the sleeve portion 12C, the motor-tool sleeve coupling 62 includes the vibrator output shaft 90A, a cylindrical boss 92, a cylindrical support member 94, an annular groove 96 within the boss 92, two counterbores 98 through the boss 92 at the bottom of the annular groove 96, an opening 100 communicating with the aspirating connector 96 and extending through the cylindrical support 94, a cylindrical opening 95 sized to receive the sleeve 18B and a brazed connection 102 more firmly fastening the boss 92 to the sleeve 18B.

The support 100 receives the vibrator shaft 90 and the boss 92 which rotationally vibrate within it and are supported by it. The groove 96 communicates with the opening 100 as it moves because of its annular shape and receives vacuum pressure which it transmits through the openings 98 into the sleeve 18B to create negative pressure in the working tip through this elongated sleeve.

With this arrangement, closing the switch 20 (FIG. 1) connects power from the power supply 132 to the oscillator 130. The vibrator 134 then vibrates at the frequency to which the oscillator 130 has been tuned by the surgeon being energized through conductors 139. The vibrator 134 reciprocates the lever 136 turning the shaft 188 repeatedly in alternating directions. This causes the lens to be impacted with the cutting edges, first in one direction tangential to the lens surface and then rapidly in the other, at an angle and speed that avoids damage to the capsular wall, if it should be near, but fragments the lens.

Because the motion is in the clockwise direction and then the counterclockwise direction, the lens is not caused to spin because the two impacts are sufficiently close in time with respect to the inertia of the lens to cancel without substantial additive acceleration of the lens in one direction from the impacts. Generally, the frequency is ultrasonic or subsonic but may be selected by the surgeon to accommodate the portion of the lens that is being fragmented by tuning the oscillator 130.

To impact the lens in opposite directions simultaneously, two side by side sets of cutting edges may be rotated in opposite directions or one set of cutting edges may be rotated in the opposite direction from the other with the one set being inside the other.

As can be understood from the above description, the technique and equipment of this invention has several advantages, such as: (1) they selectively fragment some tissue without damaging other nearby tissue; and (2) they are able to fragment, mix and aspirate tissue and in the case of cataract removal also scrub the capsular wall without damaging it, all with one instrument.

Although a preferred embodiment of the invention has been described with some particularity, many modifications and variations are possible in the preferred embodiment without deviating from the invention. Therefore, it is to be understood that within the scope of the appended claims, the invention may be practiced other than as specifically described.

What is claimed is:

1. A method comprising the steps of:

inserting a fragmenting tip having fragmenting surfaces through an opening in the eye into the lens of an eye having a cataract and a capsular wall wherein the tip has at least one movable fragmenting surface;

moving the fragmenting surface in a first direction and in at least a second direction by a shaft mounted to the fragmenting tip for movement therewith;

the step of moving the fragmenting surface in a first direction including the step of rotating the shaft within bearings wherein the fragmenting surface is rotated; and the step of moving the fragmenting surface in a second direction including the step of moving the fragmenting surface at an ultrasonic frequency;

positioning the fragmenting tip to impact the tissue of the cataract while it is moving at a velocity higher than the fragmenting velocity with respect to the capsular wall and at an angle to the cataract; whereby the cataract is fragmented but not the capsular wall; and aspirating the fragmented tissue.

2. A method in accordance with claim 1 wherein the first direction and second direction are opposite rotational directions.

3. A method according to claim 2 in which:

the step of inserting a fragmenting tip includes the substeps of: making a small incision less than 7 millimeters in diameter in the capsular sac along the margin; and inserting the fragmenting tip into the capsular sac; and the step of moving the fragmenting surface including the step of rotating the fragmenting tip to fragment a cataract.

4. A method according to claim 3 in which:

the step of rotating the fragmenting surface includes the step of rotating the fragmenting surface about a longitudinal axis of the fragmenting tip; and the step of inserting the fragmenting tip includes the step of inserting the fragmenting tip with the longitudinal axis making an acute angle with the capsular wall wherein the rotating fragmenting surface impacts the tissue of the cataract at an angle.

5. A method according to claim 1 in which the fragmenting tip is rotated with a power level of less than 1 horsepower.

6. Apparatus for removing tissue from a patient comprising:
   means for fragmenting and aspirating tissue having an operative tip;
   said means for fragmenting and separating tissue comprising means for repeatedly moving the operative tip under the control of an electrical signal at a low power level in a first direction and in at least a second direction; and at an angle to the tissue;
   said operative tip having at least one fragmenting edge with open spaces of less than 10 millimeters;
   the means for moving the fragmenting surface in a first direction including a rotatable shaft and means for rotating the rotatable shaft;
   said rotatable shaft and operative tip being connected for movement together wherein said fragmenting surface is rotated; and
   the means for moving the fragmenting surface in a second direction including means for moving the fragmenting surface at an ultrasonic frequency.

7. Apparatus in accordance with claim 6 in which the operative tip includes a cutting end and a cavitation-creating surface.

8. Apparatus according to claim 7 in which the at least one fragmenting edge includes at least two fragmenting edges and the space between fragmenting edges is less than 5 millimeters.

9. Apparatus according to claim 8 in which the operative tip has a diameter of less than 7 millimeters.

10. Apparatus according to claim 9 in which the operative tip is hollow and includes slots extending generally in a plane parallel to a longitudinal axis of the operative tip, said slots having a leading edge and a trailing edge.

11. Apparatus according to claim 10 in which the operative tip is replaceable.

12. Apparatus according to claim 6 in which the operative tip is hollow and includes slots extending generally in the plane parallel to the longitudinal axis of the operative tip, said slots having a leading edge and a trailing edge.

* * * * *